United States Patent
Scarsbrook

(10) Patent No.: US 8,277,622 B2
(45) Date of Patent: Oct. 2, 2012

(54) HIGH UNIFORMITY BORON DOPED DIAMOND MATERIAL

(75) Inventor: Geoffrey Alan Scarsbrook, Berkshire (GB)

(73) Assignee: Element Six Ltd. (GB)

( * ) Notice: Subject to any disclaimer, the term of this patent is extended or adjusted under 35 U.S.C. 154(b) by 360 days.

(21) Appl. No.: 12/523,949

(22) PCT Filed: Jan. 22, 2008

(86) PCT No.: PCT/IB2008/050214
§ 371 (c)(1),
(2), (4) Date: Sep. 10, 2009

(87) PCT Pub. No.: WO2008/090510
PCT Pub. Date: Jul. 31, 2008

(65) Prior Publication Data
US 2010/0012491 A1 Jan. 21, 2010

(30) Foreign Application Priority Data

| Jan. 22, 2007 | (GB) | 0701186.9 |
| Mar. 22, 2007 | (GB) | 0705523.9 |
| Mar. 22, 2007 | (GB) | 0705524.7 |
| May 21, 2007 | (GB) | 0709716.5 |
| Jul. 11, 2007 | (GB) | 0713464.6 |

(51) Int. Cl.
*C25B 11/04* (2006.01)
(52) U.S. Cl. ........ 204/280; 117/19; 117/929; 427/249.7
(58) Field of Classification Search .......... 204/292–294, 204/280, 290.07–290.13; 117/3, 19, 68, 117/84–109, 928, 929; 427/249.1–249.8
See application file for complete search history.

(56) References Cited

U.S. PATENT DOCUMENTS

| 5,276,338 A | 1/1994 | Beyer et al. |
| 5,491,348 A | 2/1996 | Koyamao et al. |
| 5,506,422 A | 4/1996 | Dreifus et al. |
| 5,609,926 A | 3/1997 | Prins et al. |
| 5,803,967 A | 9/1998 | Plano et al. |
| 6,013,191 A | 1/2000 | Nasser-Faili et al. |
| 6,177,292 B1 | 1/2001 | Hong et al. |
| 6,207,282 B1 | 3/2001 | Matsushita |
| 6,252,725 B1 | 6/2001 | Tran et al. |
| 6,652,763 B1 | 11/2003 | Wei et al. |
| 2004/0256624 A1 | 12/2004 | Sung |
| 2005/0109262 A1 | 5/2005 | Linares et al. |
| 2005/0127373 A1 | 6/2005 | Yokota et al. |

(Continued)

FOREIGN PATENT DOCUMENTS
EP 0343963 A2 11/1989
(Continued)

OTHER PUBLICATIONS

A.R. Lang, "The Properties of Diamond," Chapter 14 "Internal Structure," Ed. J.E. Field, Academic Press London 1979, p. 434.

(Continued)

*Primary Examiner* — J. Christopher Ball
(74) *Attorney, Agent, or Firm* — Bryan Cave LLP

(57) ABSTRACT

The present invention relates to diamond material comprising a boron doped single crystal diamond substrate layer having a first surface and a boron doped single crystal diamond conductive layer on said first surface, wherein the distribution of boron in the conductive layer is more uniform than the distribution of boron in the substrate layer.

13 Claims, 2 Drawing Sheets

U.S. PATENT DOCUMENTS

| | | | |
|---|---|---|---|
| 2006/0231015 A1 | 10/2006 | Meguro et al. | |
| 2008/0121897 A1 | 5/2008 | LaRoche et al. | |

FOREIGN PATENT DOCUMENTS

| | | | |
|---|---|---|---|
| EP | 0458530 A2 | 11/1991 | |
| EP | 0496564 A1 | 7/1992 | |
| EP | 0697738 A1 | 2/1996 | |
| EP | 0741118 A2 | 11/1996 | |
| EP | 0994074 A2 | 4/2000 | |
| EP | 1536043 A1 | 7/2005 | |
| EP | 1555337 A2 | 7/2005 | |
| EP | 1571241 A1 | 9/2005 | |
| EP | 1712661 A1 | 10/2006 | |
| GB | 2281254 A | 3/1995 | |
| GB | 2358409 A | 7/2001 | |
| GB | 2252202 A | 7/2002 | |
| GB | 2428690 A | 2/2007 | |
| JP | 60246627 A | 6/1985 | |
| JP | 2002 057167 A | 2/2002 | |
| JP | 2006 216716 A | 8/2006 | |
| WO | 99 22049 A1 | 5/1999 | |
| WO | 01 13404 A1 | 2/2001 | |
| WO | 01 75197 A1 | 10/2001 | |
| WO | 01 96633 A1 | 12/2001 | |
| WO | 01 96634 A1 | 12/2001 | |
| WO | 03 014427 A1 | 2/2003 | |
| WO | 03 052174 A2 | 6/2003 | |
| WO | 2004 027123 A1 | 4/2004 | |
| WO | 2005 074013 A2 | 8/2005 | |
| WO | 2006 013430 A1 | 2/2006 | |
| WO | 2006 061707 A2 | 6/2006 | |
| WO | 2006 117621 A1 | 11/2006 | |
| WO | 2007 066215 A2 | 6/2007 | |

OTHER PUBLICATIONS

Ariki et al., "Efficient field effect in heavily doped thin-film diamond metal-insulator-semiconductor diode employing BaTiO3 insulator film", Japanese Journal of Applied Physics, vol. 33, pp. L888-L891 (1994).

Choi et al., "Properties of natural diamond microlenses fabricated by plasma etching," Industrial Diamond Review, Issue 2, 2005, pp. 29-31.

Choi et al., "Fabrication and Evaluation of GaN Negative Bifocal Microlenses," Journal of Applied Physics, 97 (2005), 063101-1-063101-3.

Choi et al., Fabrication of natural diamond microlenses by plasma etching, J. Vac. Sci. Technol. B, 23 (2005), 130-132.

Crisman et al., "Large pyroelectric response from reactively sputtered aluminum nitride thin films," Electrochemical and Solid-State Letters, 8, 2005, pp. H31-H32.

Denisenko et al., "Diamond power devices. Concepts and Limits," Diamond and Related Materials, vol. 14, No. 3-7, pp. 491-498.

Enlund et al., "Anisotropic dry etching of boron doped single crystal CVD diamond," Carbon, 43, pp. 1839-1842.

"Ion Backscattering Analysis," in Concise Encylopedia of Material Characterization, R.W. Cahn and E. Lifshin, eds., Pergamon (London), 1993, pp. 199-204.

Karlsson et al., "Transfer of continuous-relief diffractive structure into diamond by use of inductively coupled plasma dry etching," Optics Letters, 26, 2001, pp. 1752-1754 (p. 215-217).

Karlsson et al., "Transfer of micro-optical structures into GaAs and diamond," Proceedings of the SPIE, vol. 4561, 2001, pp. 114-122.

Koide, Y., "Analysis for Electron Concentrations in n-diamond/III-nitride heterostructure and phosphorus delta-doped structure in diamond", Japanese Journal of Applied Physics, vol. 44, 2005, pp. 55-59.

Koide, Y., "Enhancement of donor ioinization in phosphorus-doped n-diamond", Applied Surface Science, col. 244, pp. 26-29 (2205).

Kondo et al., "Homoepitaxial single-crystal boron-doped diamond electrodes for electroanalysis," Journal of the Electrochemical Society, vol. 149, No. 6, Jun. 2002, pp. E179-E184.

Kondo et al., "Plasma etching treatment for surface modification of boron-dopied diamond electrodes," Electrochimica Acta, 52, 2007, 3841-3842.

Lee, et al., "Fabrication and characterization of diamond micro-optics," Diamond and Related Materials 15, 2006, pp. 725-728.

Miskys C. et al., "AIN/diamond heterojunction diodes", Applied Physics Letters, vol. 82, pp. 290-292 (2003).

Miskys C. R. et al., "Structural and interface properties of an AIN diamond ultraviolet light emitting diode", Applied Physics Letters, vol. 83, pp. 3699-3701 (2004).

Nebel C. et al., "AIN/diamond np-junctions," Diamond and Related Materials, 12, 2003, pp. 1873-1876.

Okumura, H., "Present status and future prospect of widegap semiconductor high-power devices," Japanese Journal of Applied Physics, 45, 2006, 7565-7586.

Pearton "ECR plasma etching of chemically vapour deposited diamond thin films," Electronics Letters, Apr. 1992, pp. 822-824.

Samlenski R., "Characterisation and lattice location of nitrogen and boron in homoepitaxial CVD diamond," Diamond and Related Materials, vol. 5, No. 9, Jul. 1996, pp. 947-951.

Sine et al., "Electrochemical behavior of fluorinated boron-doped diamond," Electrochemical and Solid-State Letters, 6, 2003, D9-11.

Tavares et al., "{111}-oriented diamond films and p/n junctions grown on B-doped type lb substrates," Diamond and Related Materials, vol. 14, No. 3-7, Mar. 2005, pp. 522-525.

Vogg et al., "High quality heteroepitaxial AIN films on diamond," Journal of Applied Physics, 96, 2004, 895-902.

International Search Report for PCT/IB200/050214 dated May 27, 2008.

International Search Report for PCT/IB200/050215 dated May 28, 2008.

International Search Report for PCT/IB200/050216 dated May 27, 2008.

International Search Report for PCT/IB200/050218 dated Jun. 13, 2008.

International Search Report for PCT/IB200/050219 dated Jun. 16, 2009.

UK Search Report for GB0709716.5 dated Sep. 21, 2007.
UK Search Report for GB0701186.9 dated Jul. 5, 2007.
UK Search Report for GB0705524.7 dated Jul. 16, 2007.
UK Search Report for GB0713464.6 dated Oct. 26, 2007.
UK Search Report for GB0705523.9 dated Jul. 20, 2007.

Hirakuri et al., "The Effect of Ultrasonic Vibration on CVD Diamond Nucleation," Diamond & Related Materials 6, 1997, 1031-1035.

HIGH UNIFORMITY BORON DOPED DIAMOND MATERIAL

The present invention relates to boron doped single crystal diamond material having a high uniformity, its use as an electrode and methods for producing the same.

The use of boron doped polycrystalline diamond material for electrochemical applications, in particular as an electrode in an electrochemical cell, has been well documented. For example, WO2006/013430 discloses boron doped polycrystalline diamond electrodes which comprise two layers wherein the upper layer has a lower concentration of boron and acts as a passivation layer.

There are a number of problems with such polycrystalline boron doped electrodes in certain applications, particularly in sensing or applications of quantitative measurement. The first is that in the as grown form, each grain presents surfaces with different crystallographic orientations, which can behave differently in electrochemical processes.

The second is that, even where the polycrystalline surface is processed, for example by mechanical lapping and polishing, the surface presents different growth sectors resulting from the individual grain facets during growth. The presence of a random selection of growth sectors means that boron is not incorporated uniformly during synthesis leading to huge local variations in boron concentration, which modify the local electrical conductivity and the local electrochemical behaviour. Furthermore, other impurities such as nitrogen which can electrically compensate the boron, are also taken up differently in the different growth sectors, potentially exacerbating the effect of the boron non-uniformity. Even point defects which do not contain impurities vary in concentration in the different growth sectors, again having the potential to locally modify the electrochemical behaviour of any surface prepared which intersects different growth sectors.

A final problem with such mechanically prepared flat surfaces is that the surface contains surface damage, and this can also modify the electrochemical behaviour of the material in certain highly demanding applications To date, it has been the belief that this problem is overcome by the use of single crystal diamond material. For example, US2005/0109262 describes an electrochemical synthesis electrode comprising a CVD boron doped single crystal diamond.

However, the present inventors have found that, whilst such single crystal electrodes may generally be an improvement over polycrystalline electrodes in terms of boron uniformity at the surface, many of the above problems have their counterpart in single crystal CVD diamond electrodes.

Conventionally, single crystal diamond is grown on a surface of a substrate produced by a high pressure high temperature (HPHT) process. The substrate will have dislocations running through it which break the surface upon which diamond growth will take place. When boron doped diamond is grown on the surface of the substrate by a chemical vapour deposition (CVD) technique, the dislocations breaking the surface of the substrate propagate into the CVD layer, and may cause further dislocations to form at the interface to the CVD layer, and may often then further multiply through the thickness of the grown CVD layer. As a result, the CVD diamond layer generally contains significant concentrations of dislocations and dislocation bundles or plumes.

WO2003/052174 teaches that thick layers of boron doped single crystal diamond having a low defect density and high uniformity can be synthesised by careful preparation of the substrate upon which diamond growth takes place, in particular by anisotropic etching of the growth surface of the substrate. However this approach is slow and costly, since the range of growth conditions available is limited by the need to avoid the formation of pits. Under less well controlled conditions, where the diamond is grown to relatively large thicknesses, pits are often present on the as-grown surface of the diamond above and around the dislocation bundles. The pits expand in size as the thickness of the growing layer increases, causing the enlargement of the areas of non-uniform boron uptake and the proportion of the surface having a boron concentration and hence electrical conductivity that differs from the rest of the surface.

The present inventors have identified that the pits which form on the (001) growth surface, which are typically square or octagonal, are comprised of one of, or a mixture of, $\{111\}$ and $\{110\}$ surfaces which constitute different growth sectors. The uptake of boron during growth of single crystal diamond on the substrate varies between different growth sectors. Based on studies of boron uptake in primary growth sectors, the expectation would be that such $\{110\}$ and particularly $\{111\}$ surfaces would take up higher levels of boron than the $\{100\}$ growth sector, but within such pits it is surprisingly found that the boron uptake is generally lower in these growth sectors. Although the explanation for the difference is not known, without wishing to be bound by any particular theory, two possible reasons are that the surface step morphology within the pit is affected or it is because of depletion of the boron in the source gas in the confined space within the pit.

The presence of pits which cause a variation in the local surface conductivity is a particular problem where a thick boron doped single crystal CVD diamond is grown and then is multiply sliced to male a series of thinner plates, since the extent of the spatial non-uniformity of the boron concentration will vary between plates, being least in regions originally adjacent to the plate upon which the thick layer was grown and most in regions that were originally furthest away. Any variation in the average boron concentration through the thickness of the thick layer, another common problem, is also detrimental.

As described above, the presence of the pits thus means that there is a huge local variation in boron concentration at the as-grown surface of the single crystal diamond material. Processing the material by anisotropic etching prior to synthesis in the manner described in WO2003/052174 exacerbates the problem as it introduces further pitting into the substrate surface before CVD growth starts. This can make the material even less suitable for use in electrochemical analytical applications.

In any electrochemical sensor, there are two key components. The first is the surface presented to the fluid under processing or analysis (hereinafter referred to as the "electrolyte"). The second key component is the electrical connection or connections to the device. Preferably such a connection is made on the reverse side of the electrode structure, such that the contact is well separated from the region in contact with the electrolyte, which is often aggressive. Since the electrode needs some mechanical integrity, and in addition would ideally provide a uniform potential to the electrochemically active surface, the total electrode thickness needs to be significant (e.g. typically >100 µm, more typically >300 µm for electrodes with lateral dimensions of >1 mm). Electrical connection can then be made by either a) making the whole thickness of the diamond layer conductive, b) bonding a thin conductive diamond layer onto a non-diamond substrate which provides the electrical contact, or c) drilling a hole through a non-conductive backing layer, which may be a diamond backing layer, to enable contact to be made with the back surface of a front conductive layer. Solution (a) suffers from the problems described above, whilst solutions (b) and (c) are complex and costly to manufacture in bulk, and often fragile in use.

There is hence a need for diamond material which does not suffer from the disadvantages described above, specifically which is suitable for use in electrochemical analytical applications and to which electrical contacts can be easily attached without affecting its performance.

In a first aspect, the present invention provides diamond material comprising a boron doped single crystal diamond substrate layer having a first surface and a boron doped single crystal diamond conductive layer on said first surface, wherein the distribution of boron in the conductive layer is more uniform than the distribution of boron in the substrate layer.

In a second aspect, the present invention provides diamond material comprising a boron doped single crystal diamond substrate layer having a first surface and a boron doped single crystal diamond conductive layer on said first surface, wherein the electrical conductivity of the conductive layer is more uniform than the electrical conductivity of the substrate layer.

The term "substrate layer" will be used hereinafter to refer to the boron doped single crystal diamond substrate layer having a first surface of the diamond material of the present invention.

The term "uniformly conductive layer" will be used hereinafter to refer to the boron doped single crystal diamond conductive layer of the diamond material of the present invention.

As a consequence of the high uniformity of boron concentration and/or uniform electrical conductivity of the external surface of the diamond material, the material of the present invention is particularly useful as an electrode where at least a part of the exposed surface of the uniformly conductive layer forms the major working surface of the electrode.

In a third aspect, the present invention provides an electrode comprising diamond material of the present invention.

Advantageously, because it has a two layer structure, each layer comprising boron doped diamond, the electrode of the present invention does not suffer from the problems associated with conventional diamond electrodes. More specifically, as a consequence of its two layer construction, it is only the properties of the exposed surface of the uniformly conductive layer which determine the properties of the overall device as it is this surface which, in use, forms a major working surface of the electrode. Thus the present inventors have found that, surprisingly, provided that there is a uniform concentration of boron across the working surface of the electrode, it is not necessary for the concentration of boron to be uniform throughout the material. This means that the bulk of the diamond material which forms the electrode can be synthesised under less stringent conditions with the result that thick layers can be grown quickly and in a more cost effective manner.

The term "major working surface" as used herein refers to the surface of the electrode which will be in direct contact with the electrolyte when in use. In sensing electrodes, generally only one surface of the electrode structure is in contact with the electrolyte. In the case of processing electrodes, a bipolar configuration may be used where opposing major working surfaces will form the anode and cathode when in use; in such a configuration one or both surfaces may have the additional uniformly doped boron layer. For example, in the case of a flat electrode which is rectangular, the major working surfaces will be the rectangular faces as illustrated in FIG. 1a. In the case of a disc shaped electrode, it is the two circular faces of the electrode which form the major working surfaces as illustrated in FIG. 1b.

Preferably the major working surfaces of the electrode have a surface area of greater than about 0.3 $mm^2$, preferably greater than about 1 $mm^2$, preferably greater than about 4 $mm^2$, preferably greater than about 10 $mm^2$, preferably greater than about 25 $mm^2$, preferably greater than about 50 $mm^2$, preferably greater than about 100 $mm^2$, preferably greater than about 200 $mm^2$, preferably greater than about 400 $mm^2$.

The distribution of boron is preferably uniform over at least about 40%, preferably at least about 50%, preferably at least about 60%, preferably at least about 75%, preferably at least about 85%, preferably at least about 90%, preferably at least about 95%, preferably at least about 98% of the major working surface of the electrode.

Electrodes according to the present invention are particularly useful for analytical and sensing applications, in which even a small variation in conductivity across the surface can cause problems. Thus in a farther aspect, the present invention provides for the use of electrodes as defined above in electrochemical analytical and sensing applications.

According to a farther aspect, the present invention further provides a method for producing an electrode comprising processing a surface of a substrate layer of boron-doped single crystal diamond to a surface roughness $R_q$ of about 1 µm or less, preferably about 0.1 µm or less, preferably about 0.05 µm, preferably about 0.02 µm or less, preferably about 0.01 µm or less; and growing a second layer of single crystal boron doped diamond on the surface of the substrate layer of boron doped single crystal diamond material.

Alternatively the surface of the substrate layer may be processed such that a depth of material is removed from the whole surface that is greater than the depth of the deepest pit on the surface. The approximate depth of the deepest pit on the surface of the substrate layer can be determined using conventional light microscopy techniques. The presence of pits may be determined using conventional reflected light microscopy at a total magnification of between about 20 times and about 100 times. It is thus straightforward to determine when sufficient depth of material has been removed from the surface.

By processing a surface of the substrate layer of boron doped single crystal diamond to a surface roughness $R_q$ of about 1 µm or less, preferably about 0.1 µm or less, preferably about 0.05 µm, preferably about 0.02 µm or less, preferably about 0.01 µm or less, any pits which have formed during growth around dislocation bundles in the substrate layer of boron doped single crystal diamond will have been removed or largely removed so that the processed surface presents a single growth sector to the growth environment used for depositing the second layer which will be uniformly conductive. More specifically, the processed surface is such that any further growth thereon will be a single growth sector. In this way, the previously existing pits are not propagated in to the subsequently grown layer of boron doped single crystal diamond layer. This means that the as-grown surface of the second layer of boron doped single crystal diamond has a high uniformity of boron concentration and is much more uniformly electrically conductive. The overall method is simple and cost effective.

While the average concentration of boron in the substrate layer of the diamond material of the present invention should be sufficient to maintain conductivity between the two layers of boron doped single crystal diamond material, it is not crucial that the dispersion of boron within the substrate layer is uniform. The average concentration of boron in the substrate layer is preferably about $1\times10^{17}$ atoms/cm$^3$ or more, preferably about $1\times10^{18}$ atoms/cm$^3$ or more, preferably about $1\times10^{19}$ atoms/cm$^3$ or more, preferably about $3\times10^{19}$ atoms/cm$^3$ or more, preferably about $1\times10^{20}$ atoms/cm$^3$ or more. The average concentration of boron in the substrate layer is preferably about $1\times10^{22}$ atoms/cm$^3$ or less, preferably about $8\times10^{21}$ atoms/cm$^3$ or less, preferably about $1\times10^{21}$ atoms/cm$^3$ or less, preferably about $5\times10^{20}$ atoms/cm$^3$ or less. The average concentration of boron in the substrate layer of boron doped single crystal diamond is preferably in the range from about $10^{17}$ atoms/cm$^3$ to about $1\times10^{22}$ atoms/cm$^3$. Preferably the average concentration of boron in the substrate layer is in the range from about $10^{18}$ atoms/cm$^3$ to about $8\times10^{21}$ atoms/cm$^3$. Preferably the average concentration of boron in the substrate layer is in the range from about $10^{19}$ atoms/cm$^3$ to about $5\times10^{21}$ atoms/cm$^3$. Preferably the average concentration of boron in the substrate layer is higher than the average concentration of boron in the uniformly conductive layer, or the thickness of the uniformly conductive layer is greater than the characteristic dimension over which the boron concentration varies in the substrate layer (e.g. the average pit dimension), or preferably both these conditions hold.

The electrical conductivity of the two layers of the diamond material of the present invention can be determined by measuring the electrical resistivity at room temperature (300 K) and then using the conversion:

Conductivity($J$)=1/resistivity($\rho$)

The resistivity of a material can be calculated by measuring the surface resistance and converting the value obtained to a bulk resistivity measurement.

For instance, when using a four point probe, the surface resistance may be measured by contacting two electrodes with the surface(s) in question at two points separated by a specified distance. A voltage is then applied between the two electrodes. The voltage required to drive a fixed current is measured which allows determination of the surface resistance using Ohm's law, specifically:

$R=V/I$ where V is the voltage difference between the two measurement points and I is the forced current flowing between the two measurement points.

An example of a suitable apparatus for determining this measurement is a Jandel Cylindrical hand held Four point Probe in combination with a suitable meter such as a TTi BS407 Precision Milli/Micro Ohm meter.

The surface resistance measured can be used to calculate the electrical resistivity of the material using the relationship:

$\rho=R\pi t/\ln 2$ where t is the thickness of the diamond material in μm and R is the resistance determined as defined above in mΩ.

In general, the resistivity values are not corrected for either the spacing of the measurement points being similar to the thickness of the diamond material nor for the fact that some of the measurements are being made close to the edge of the sample where the theory assumes a semi infinite plane.

The term "electrical conductivity" as used herein refers to the electrical conductivity of the material at 300 K.

The electrical conductivity of the substrate layer is preferably about $1\times10^{-4}$ Ω$^{-1}$cm$^{-1}$ or more, preferably about $2\times10^{-4}$ Ω$^{-1}$cm$^{-1}$ or more, preferably about $5\times10^{-4}$ Ω$^{-1}$cm$^{-1}$ or more, preferably about $1\times10^{-3}$ Ω$^{-1}$cm$^{-1}$ or more, preferably about $5\times10^{-3}$ Ω$^{-1}$cm$^{-1}$ or more, preferably about $1\times10^{-2}$ Ω$^{-1}$cm$^{-1}$ or more, preferably about $5\times10^{-2}$ Ω$^{-1}$cm$^{-1}$ or more, preferably about $1\times10^{-1}$ Ω$^{-1}$cm$^{-1}$ or more.

The electrical conductivity of the substrate layer is preferably about $5\times10^{3}$ Ω$^{-1}$cm$^{-1}$ or less, preferably about $2\times10^{3}$ Ω$^{-1}$cm$^{-1}$ or less, preferably about $1\times10^{3}$ Ω$^{-1}$cm$^{-1}$ or less, preferably about $5\times10^{2}$ Ω$^{-1}$cm$^{-1}$ or less, preferably about $2\times10^{2}$ Ω$^{-1}$cm$^{-1}$ or less, preferably about $1\times10^{2}$ Ω$^{-1}$cm$^{-1}$ or less.

The electrical conductivity of the substrate layer is preferably in the range from $1\times10^{-4}$ Ω$^{-1}$cm$^{-1}$ to about $1\times10^{2}$ Ω$^{-1}$cm$^{-1}$, preferably from about $5\times10^{-4}$ Ω$^{-1}$cm$^{-1}$ to about $2\times10^{2}$ Ω$^{-1}$cm$^{-1}$, preferably from about $2\times10^{-4}$ Ω$^{-1}$cm$^{-1}$ to about $5\times10^{2}$ Ω$^{-1}$cm$^{-1}$, preferably from about $1\times10^{-3}$ Ω$^{-1}$cm$^{-1}$ to about $1\times10^{3}$ Ω$^{-1}$cm$^{-1}$, preferably from about $5\times10^{-3}$ Ω$^{-1}$cm$^{-1}$ to about $2\times10^{3}$ Ω$^{-1}$cm$^{-1}$, preferably from about $1\times10^{-2}$ Ω$^{-1}$cm$^{-1}$ to about $5\times10^{3}$ Ω$^{-1}$cm$^{-1}$.

The average concentration of boron present in the substrate layer of boron doped single crystal diamond may be determined by any technique used conventionally in the art. An example of a suitable technique is secondary ion mass spectrometry (SIMS). SIMS is a very sensitive technique which can be used to perform elemental analysis of thin layers, typically in the range of a few nm to a few μm. In particular SIMS has a very high sensitivity to boron and boron levels as low as about $10^{13}$ cm$^{-3}$ can be measured in diamond and measurements are typically reproducible to better than about ±5%. In this technique, the surface is sputtered by rastering a primary ion beam, typically an O$_2$$^+$ ion beam accelerated to an energy about 5 keV, across a small area, for example an area of about 30 μm×about 30 μm, and the portion of sputtered material that leaves the surface as ions is analysed by mass spectrometry. By comparing the count rate of a particular species to a standard concentration and by determining the depth of the sputter hole, a profile of depth versus concentration can be generated. A set of values can be taken in a given area and then averaged. Typically multiple measurements are made at a series of points arranged as a grid on the surface; for example on a 2 mm×2 mm plate, SIMS measurements might be made on a rectilinear array every 200 μm, giving a total of about 100 measurements. The arithmetical average of the measurements is determined and the spread of results can be used to give a quantitative measure of the uniformity.

As the skilled person will appreciate, it is not possible to record a measurement at a single point and there will always be an area associated with the point. Thus the term "point" as used herein refers to, the approximate centre of each of the areas over which the specific measurement is taken. The area over which each measurement is taken is preferably about 100 μm×about 100 μm, more preferably about 75 μm×about 75 μm, more preferably about 50 μm×about 50 μm, more preferably about 30 μm by about 30 μm.

The electrical conductivity of the uniformly conductive layer is preferably about $1\times10^{-4}$ Ω$^{-1}$cm$^{-1}$ or more, preferably about $5\times10^{-4}$ Ω$^{-1}$cm$^{-1}$ or more, preferably about $2\times10^{-4}$ Ω$^{-1}$cm$^{-1}$ or more, preferably about $1\times10^{-3}$ Ω$^{-1}$cm$^{-1}$ or more, preferably about $5\times10^{-3}$ Ω$^{-1}$cm$^{-1}$ or more, preferably about $1\times10^{-2}$ Ω$^{-1}$cm$^{-1}$ or more, preferably about $5\times10^{-2}$ Ω$^{-1}$cm$^{-1}$ or more, preferably about $1\times10^{-1}$ Ω$^{-1}$cm$^{-1}$ or more.

The electrical conductivity of the uniformly conductive layer is preferably about $5\times10^{3}$ Ω$^{-1}$cm$^{-1}$ or less, preferably about $2\times10^{3}$ Ω$^{-1}$cm$^{-1}$ or less, preferably about $1\times10^{3}$ Ω$^{-1}$cm$^{-1}$ or less, preferably about $5\times10^{2}$ Ω$^{-1}$cm$^{-1}$ or less, preferably about $2\times10^{2}$ Ω$^{-1}$cm$^{-1}$ or less, preferably about $1\times10^{2}$ Ω$^{-1}$cm$^{-1}$ or less.

The electrical conductivity of the uniformly conductive layer is preferably in the range from $1\times10^{-4}$ Ω$^{-1}$cm$^{-1}$ to about $1\times10^{2}$ Ω$^{-1}$cm$^{-1}$, preferably from about $5\times10^{-4}$ Ω$^{-1}$cm$^{-1}$ to about $2\times10^2$ $\Omega^{-1}\text{cm}^{-1}$, preferably from about $2\times10^{-4}$ $\Omega^{-1}\text{cm}^{-1}$ to about $5\times10^2$ $\Omega^{-1}\text{cm}^{-1}$, preferably from about $1\times10^{-3}$ $\Omega^{-1}\text{cm}^{-1}$ to about $1\times10^3$ $\Omega^{-1}\text{cm}^{-1}$, preferably from about $5\times10^{-3}$ $\Omega^{-1}\text{cm}^{-1}$ to about $2\times10^3$ $\Omega^{-1}\text{cm}^{-1}$, preferably from about $1\times10^{-2}$ $\Omega^{-1}\text{cm}^{-1}$ to about $5\times10^3$ $\Omega^{-1}\text{cm}^{-1}$.

The uniformity of the electrical conductivity at the working surface of the uniformly conductive layer can be measured by using an atomic force microscope ("AFM") in "conductivity mode". By the use of this method, a spatially-resolved map of the electrical conductivity (a "conductivity map") of the surface may be obtained on a scale that is relevant to the problem previously described.

Both of the above techniques (SIMS and AFM) can also be applied to a prepared cross-section of the electrode to, for example, characterise the thickness of the uniformly conductive layer and its average boron concentration directly in comparison to the first layer. General characterisation of the spatial arrangement of the two layer structure can also be completed on the cross-section using photoluminescence or cathodoluminescence, for example using a DiamondView™ instrument.

A key function of the substrate layer is to provide a substrate for the uniformly conductive layer, an external surface of which will form the major working surface of the electrode. This means that, for example, contacts can be attached to the substrate layer without damaging the uniformly conductive layer and thus without impairing performance. In this regard, the substrate layer preferably has a thickness of about 50 µm or more, preferably about 75 µm or more, preferably about 100 µm or more, preferably about 150 µm or more, preferably about 200 µm or more. The substrate layer preferably has a thickness of about 1000 µm or less, preferably about 700 µm or less, preferably about 500 µm or less, preferably about 400 µm or less.

The substrate layer may be natural single crystal Type IIb diamond, high pressure high temperature (HPHT) synthetic single crystal Type IIb diamond or single crystal boron doped CVD diamond. Preferably the substrate layer is single crystal boron doped CVD diamond. Preferably the substrate has major faces that are within about 10°, preferably within about 5° of the [001] direction. If the substrate layer is a single crystal boron doped CVD diamond, it may be a substrate layer that has itself been grown on a single crystal diamond plate of any kind known in the art, but preferably on an HPHT synthetic single crystal Type Ib diamond or a single crystal CVD diamond; preferably the plate has major faces that are within about 10°, preferably within about 5° of the [001] direction.

In the diamond material of the present invention, the substrate layer is in contact with the uniformly conductive layer. Where the substrate layer is synthetic single crystal diamond, the internal contact surface of the substrate layer will be the surface of the substrate layer processed as previously described.

Preferably the internal contact surface of the substrate layer has been processed, preferably mechanically processed and/or etched. The location of the interface between the substrate and the uniformly conductive layer is distinguishable by a sharp change in uniformity of the distribution of boron as measured by SIMS or imaged using a DiamondView™ instrument.

The uniformly conductive layer of the material of the present invention will, where the diamond material of the present invention is used as an electrode, form a major working surface of the electrode. The uniformly conductive layer preferably has a thickness of about 100 µm or less, preferably about 80 µm or less, preferably about 60 µm or less, preferably about 40 µm or less. The uniformly conductive layer preferably has a thickness of about 0.2 µm or more, 0.5 µm or more, preferably about 1 µm or more, preferably about 3 µm or more, preferably about 5 µm or more, preferably about 10 µm or more.

The average concentration of boron in the uniformly conductive layer is preferably in the range from about $10^{17}$ atoms/cm$^3$ to about $1\times10^{22}$ atoms/cm$^3$. Preferably, the average concentration of boron in the uniformly conductive layer is in the range from about $10^{18}$ atoms/cm$^3$ to about $8\times10^{21}$ atoms/cm$^3$. Preferably, the average concentration of boron in the uniformly conductive layer is in the range from about $10^{19}$ atoms/cm$^3$ to about $5\times10^{21}$ atoms/cm$^3$. Preferably, the average concentration of boron in the uniformly conductive layer is in the range from about $10^{19}$ atoms/cm$^3$ to about $3\times10^{21}$ atoms/cm$^3$. By ensuring that the average concentration of boron is in the specified range, the conductivity of the uniformly conductive layer will be appropriate for its use as an electrode, in particular in sensing applications.

The uniformly conductive layer will generally have been grown directly on to the processed surface of the substrate layer wherein the substrate layer provides the substrate for synthesis of the uniformly conductive layer. The external surface of the uniformly conductive layer is generally the as-grown surface, which may optionally have been subjected to further processing steps. Where the diamond material of the present invention is used as an electrode, the external surface of the uniformly conductive layer forms a major working surface of the electrode.

The distribution of boron in the uniformly conductive layer is more uniform than the distribution of boron in the substrate layer.

Preferably the uniformity of the distribution of boron in the uniformly conductive layer is such that, for 20 or more measurements, preferably for 30 or more measurements, preferably for 40 or more measurements, the standard deviation of the boron concentrations measured divided by the mean of the boron concentrations measured is about ½, preferably about ⅓, more preferably about ¼, more preferably about ⅕, more preferably about ⅙ of the standard deviation divided by the mean, for 20 or more measurements, preferably for 30 or more measurements, preferably for 40 or more measurements, of the boron concentration of the substrate layer.

In a preferred embodiment, the uniformity of the distribution of boron in the uniformly conductive layer is such that, for 20 or more measurements, preferably for 30 or more measurements, preferably for 40 or more measurements, the standard deviation of the boron concentrations measured divided by the mean of the boron concentrations measured is less than about 80%, preferably less than about 60%, preferably less than about 40%, preferably less than about 30% of the standard deviation divided by the mean, for 20 or more measurements, preferably for 30 or more measurements, preferably for 40 or more measurements, of the boron concentration of the substrate layer.

The uniformity of the boron distribution in the substrate layer is preferably measured after the substrate layer has been processed to remove the pits resulting from its synthesis but before the uniformly conductive layer is deposited on top of the substrate layer. The uniformity of the boron distribution in the uniformly conductive layer may be measured before or after any post-deposition processing. If any post-deposition processing is performed, it is preferable that the uniformity of the boron distribution in the uniformly conductive layer is measured after any post-deposition processing. It is also possible to characterise the uniformity of the substrate layer by careful removal of the uniform layer, for example by mechanical means.

The uniformity of the boron concentration is measured as follows. The technique of SIMS is used to measure the uniformity of the boron concentration in the substrate layer and in the uniformly conductive layer. Typically multiple SIMS measurements are made at a series of points arranged as a grid on the surface. For example on a 2 mm×2 mm plate, SIMS measurements might be made on a rectilinear array every about 200 µm, giving a total of about 100 measurements. The arithmetical average of the measurements is determined and the spread of results can be used to give a quantitative measure of the uniformity. To obtain a meaningful measure of the uniformity of the boron concentration, measurements should be made at 20 or more points, preferably at 30 or more points, preferably at 50 or more points. The spacing between points should be no greater than about 500 µm, preferably no greater than about 350 µm, preferably no greater than about 250 µm.

In order to ensure that the diamond material of the present invention is particularly suited for electrochemical sensing applications, the uniformly conductive layer has a high uniformity of boron at its external surface. More specifically, preferably about 75% or more, preferably about 80% or more, preferably about 85% or more, preferably about 90% or more of the values for the concentration of boron measured over a grid of 20 or more, preferably 30 or more, preferably 50 or more, points on the external surface of the uniformly conductive layer are within ±30%, preferably within ±25%, preferably within ±20%, preferably within ±15%, preferably within ±10%, of the mean of the concentration values measured.

Alternatively and/or in addition, the electrical conductivity of the uniformly conductive layer is more uniform than the electrical conductivity of the substrate layer.

Preferably the uniformity of the electrical conductivity of the uniformly conductive layer is such that, for 20 or more measurements, preferably for 30 or more measurements, preferably for 40 or more measurements, the standard deviation of the electrical conductivities measured divided by the standard deviation of the electrical conductivities measured is about ½, preferably about ⅓, more preferably about ¼, more preferably about ⅕, more preferably about ⅙ of the standard deviation divided by the mean, for 20 or more measurements, preferably for 30 or more measurements, preferably for 40 or more measurements, of the electrical conductivities of the substrate layer.

In a preferred embodiment, the uniformity of the electrical conductivities of the uniformly conductive layer is such that, for 20 or more measurements, preferably for 30 or more measurements, preferably for 40 or more measurements, the standard deviation of the electrical conductivities measured divided by the mean of the electrical conductivities measured is less than about 80%, preferably less than about 60%, preferably less than about 40%, preferably less than about 30% of the standard deviation divided by the mean, for 20 or more measurements, preferably for 30 or more measurements, preferably for 40 or more measurements, of the electrical conductivities of the substrate layer.

The uniformity of the electrical conductivity of the substrate layer is preferably measured after the substrate layer has been processed to remove the pits resulting from its synthesis but before the uniformly conductive layer is deposited on top of the substrate layer. The uniformity of the electrical conductivity in the uniformly conductive layer may be measured before or after any post-deposition processing. If any post-deposition processing is performed, it is preferable that the uniformity of the electrical conductivity in the uniformly conductive layer is measured after any post-deposition processing. It is also possible to characterise the uniformity of the substrate layer by careful removal of the uniform layer, for example by mechanical means.

The diamond material of the present invention may further comprise a third layer of boron doped single crystal diamond wherein the third layer is in contact with the bottom external surface of the substrate layer. The third layer may be the same or different in composition to the uniformly conductive layer provided that it satisfies the features as defined above in relation to the uniformly conductive layer. Where this is the case, an electrode formed from such material may have two major working surfaces thus maximising the surface area presented for chemical reactions and making it particularly suitable for use as a bipolar electrode.

Advantageously, the diamond material of the present invention is used to form an electrode which has an improved spatial uniformity of response.

The electrodes of the present invention may be used in a number of different configurations.

An electrode of the present invention may be used as an electrode for monitoring or measuring an electrochemical process. The electrode may be used in an electrochemical cell with a standard electrode (for example a calomel electrode or a standard hydrogen electrode) as a counter electrode. A constant electrical potential may be applied between the electrode of the present invention and the standard electrode and the current (which is proportional to the reaction rate) measured as a function of time. Alternatively the electrical potential between the electrode of the invention and the standard electrode is swept around a cycle (e.g. from +5 V to −5 V and back to +5 V) and the resultant current or current density is measured, a process known in the art as cyclic voltammetry.

In another example, two electrodes of the present invention may be immersed in a liquid to be treated such that the major working surfaces are parallel and adjacent to one another. Generally, in such an arrangement, the major working surfaces are separated by a distance in the range from 1 mm to 200 mm, depending on the specific application. A potential difference of between 0.5 V to 20 V is typically applied between the electrodes by means of an external circuit.

Alternatively, where the electrode has two major working surfaces, a plurality of electrodes of the present invention may be arranged parallel and adjacent to each other to form an electrode stack. A stack of electrodes may comprise between 3 and 200 electrodes. The separation between the major working surfaces of adjacent electrodes in the stack is typically in the range from 1 mm to 200 mm. A potential difference is applied between the first and last electrodes in the stack. In this case, it may be arranged so that the liquid to be electrolysed flows in a serpentine manner between the first and second electrodes, then between the second and third electrodes and so on until it has passed through the whole reactor, such that the spaces between the electrodes effectively lie in series to increase the treatment time of a particular volume. Alternatively, the spaces between the electrodes may effectively be used in parallel so as to increase the volume of liquid treated.

In either case, the flow between the first and second and second and third electrodes, and so on, does not provide a "short circuit" for electrical current, since the impedance of the current path through the liquid is designed to be substantially greater than that through the electrodes.

The electrode of the present invention may be used as an anode, a cathode or a bipolar electrode. Preferably the electrode of the present invention is used as an anode.

Alternatively only regions of the uniformly conductive layer may be exposed to the electrolyte, as for example in a microelectrode array.

The present invention also relates to an electrochemical cell comprising an electrode as defined herein and, in addition, to use of an electrode as defined herein in a sensing application.

The electrode of the present invention may be produced by a simple and cost effective method. In this regard, the present invention further provides a method for producing an electrode comprising (a) processing a surface of a substrate layer of boron-doped single crystal diamond to a surface roughness $R_q$ of about 1 μm or less; and (b) growing a second layer of single crystal boron-doped diamond on the surface of the substrate layer to produce a boron doped single crystal diamond electrode.

The second layer of single crystal boron doped diamond preferably has a thickness of about 100 μm or less, preferably about 50 μm or less, preferably about 25 μm or less.

The substrate layer may be natural IIb diamond, high pressure high temperature (HPHT) synthetic IIb diamond or boron doped CVD diamond. Preferably the substrate layer is boron doped CVD diamond.

In the first step of the method of the present invention, a surface of a substrate layer of boron doped single crystal diamond is processed to a surface roughness $R_q$ of about 1 μm or less, preferably about 0.1 μm or less, preferably about 0.05 μm, preferably about 0.02 μm or less, preferably about 0.01 μm or less. Where the substrate layer is synthetic diamond, the surface of the substrate layer which is processed in step (a) will generally be the as-grown surface of the substrate layer. Any technique used conventionally in the art may be employed in this step. Preferably the surface of the substrate layer is mechanically processed by, for example, scaifing, polishing or lapping.

Preferably the surface of the substrate layer is processed to a surface roughness $R_q$ of about 1 μm or less, preferably about 0.1 μm or less, preferably about 0.05 μm, preferably about 0.02 μm or less, preferably about 0.01 μm or less.

Advantageously, where step (a) involves mechanical processing, after processing in step (a) and before growth in step (b), the surface of the substrate layer is subjected to an isotropic etching step.

Etching means the removal of a minimum thickness of material from the mechanically processed surface of step (a), based on grit size of the mechanical process of step (a) to provide a surface which is substantially free of damage caused by the mechanical processing itself. An isotropic etch is one which does not substantially increase the surface roughness of the surface.

Surface roughness measurements $R_q^B$ and $R_q^A$ are taken on the same area of the diamond. By "same area" is meant an equivalent area as close as reasonably practical, using multiple measurements and statistical analysis where necessary to verify the general validity of the measurements, as is known in the art. In particular, where an isotropic etch step is included, the isotropically etched surface of the substrate layer has a roughness $R_q^A$ (After the etch) and the original surface a roughness $R_q^B$ (Before the etch), such that $R_q^A/R_q^B$ is preferably less than 1.5, more preferably less than 1.4, more preferably less than 1.2, more preferably less than 1.1.

In addition, preferably the etched surface is smoother than the initially prepared surface of step (a), and in particular, preferably the $R_q$ of the etched surface ($R_q^A$) is preferably about 10 nm or less, preferably about 5 nm or less, preferably about 2 nm or less, preferably about 1 nm or less, preferably about 0.5 nm or less, preferably about 0.3 nm or less.

Where an isotropic etching step is included, preferably the thickness of material removed exceeds about 0.2 μm or more, more preferably about 0.5 μm or more, more preferably about 1.0 μm or more, more preferably about 2 μm or more, more preferably about 5 μm or more, more preferably about 10 μm or more.

Removal, by etching, of a minimum thickness of material from the as mechanically processed surface of the substrate layer formed in step (a) of the method of the present invention based on grit size of last mechanical process, to provide a surface which is free or substantially free of mechanical processing damage, requires the removal of sufficient depth to significantly reduce the surface damage. It thus needs removal by etching of the same order of thickness as the surface damage layer. Typically surface damage layers have thicknesses in the range of about 0.2 μm to about 20 μm (or thicker with very aggressive lapidary techniques). Thus, preferably the etch removes a thickness of material from the surface, where the thickness of material removed is at least about 0.2 μm, more preferably at least about 0.5 μm, more preferably at least about 1.0 μm, more preferably at least about 2 μm, more preferably at least about 5 μm, more preferably at least about 10 μm. The surface damage layer typically has a thickness that is about the same as the size of the largest diamond grit particle used for the last stage of mechanical processing in step (a); for example a surface scaife polished with 1-2 μm sized diamond grit will typically have a surface damage layer about 2 μm thick. Therefore, to minimise the amount of damage from mechanical processing that remains after etching, the amount of material removed is preferably at least 0.2 times the size of the largest grit particles, more preferably at least 0.5 times the size of the largest grit particles, more preferably at least 0.8 times the size of the largest grit particles, more preferably at least 1.0 times the size of the largest grit particles, more preferably at least 1.5 times the size of the largest grit particles, more preferably at least 2 times the size of the largest grit particles.

After the etch, the surface of the substrate layer of boron doped single crystal diamond preferably has a surface roughness after the etch, $R_q$, of less than 10 nm, more preferably less than 5 nm, more preferably less than 2 nm, more preferably less than 1 nm, more preferably less than 0.5 nm, more preferably less than 0.3 nm.

Where the surface is formed by etching it can extend across the whole of a surface of the diamond layer, or across a proportion of the surface such as structural features etched into the surface, using known techniques such as photolithography, this portion of the surface then forming the surface, per se.

In step (b), a second layer of boron doped single crystal diamond material is grown on the surface of the substrate layer which has been processed in step (a). Advantageously, because the surface of the substrate layer has been processed in step (a), the resulting second layer has a high uniformity of boron concentration on its as-grown surface, making it particularly useful for sensing applications.

Preferably the substrate layer of boron doped single crystal diamond is boron doped CVD diamond. Where this is the case, it is preferable that the substrate layer of boron doped CVD is produced by providing a diamond substrate having a surface which is substantially free of crystal defects, providing a source gas including a source of boron, dissociating the source gas and allowing homoepitaxial diamond growth on the surface of the substrate which is substantially free of crystal defects.

In order to control the morphology of the growing diamond, the source gas may further comprise nitrogen in an amount in the range from about 0.5 ppm to about 10000 ppm, preferably about 1 ppm to about 1000 ppm, preferably form about 3 ppm to about 200 ppm.

The boron source may be $B_2H_6$ although other gaseous, liquid/vapour or solid sources may be used.

The gas mixture used in the synthesis process may contain any gases known in the art and will contain a carbon-containing material which dissociates producing radicals or other reactive species. The gas mixture will also generally contain gases suitable to provide hydrogen or a halogen in atomic form.

The substrate will generally be synthetic, natural or CVD diamond. Preferably the substrate is a low birefringence type Ia or IIb natural, Ib or IIa high pressure/high temperature synthetic diamond or a CVD synthesised single crystal diamond.

The defect density of the substrate is most easily characterised by optical evaluation after using a plasma or chemical etch optimised to reveal the defects. The surface of the substrate upon which homoepitaxial growth occurs preferably has a density of surface etch features related to defects of below about $5 \times 10^3$/mm, preferably below about $10^2$/mm.

One specific method of minimising the surface damage of the substrate, is to include an in situ plasma etch on the surface on which the homoepitaxial diamond growth is to occur. In principle this etch need not be in situ, nor immediately prior to the growth process, but the greatest benefit is achieved if it is in situ, because it avoids any risk of further physical damage or chemical contamination. An in situ etch is also generally most convenient when the growth process is also plasma based. The plasma etch can use similar conditions to the deposition or diamond growing process, but with the absence of any carbon containing source gas and generally at a slightly lower temperature to give better control of the etch rate. For example, it can consist of one or more of:

(i) an oxygen etch using predominantly hydrogen with optionally a small amount of Ar and a required small amount of $O_2$. Typical oxygen etch conditions are pressures of $50-450 \times 10^2$ Pa, an etching gas containing an oxygen content of 1 to 4 percent, an argon content of 0 to 30 percent and the balance hydrogen, all percentages being by volume, with a substrate temperature about 600° C. to about 1100° C. (more typically about 800° C.) and a typical duration of 3 to 60 minutes;

(ii) a hydrogen etch which is similar to (i) but where the oxygen is absent; or (iii) alternative methods for the etch not solely based on argon, hydrogen and oxygen may be used, for example, those utilising halogens, other inert gases or nitrogen.

Typically the etch consists of an oxygen etch followed by a hydrogen etch and then moving directly into synthesis by the introduction of the carbon source gas.

The etch time/temperature is selected to enable any remaining surface damage from processing to be removed, and for any surface contaminants to be removed, but without forming a highly roughened surface and without etching extensively along extended defects (such as dislocations) which intersect the surface and thus causing deep pits. As the etch is aggressive, it is particularly important for this stage that the chamber design and material selection for its components be such that no chamber material is transferred by the plasma into the gas phase or to the substrate surface. The hydrogen etch following the oxygen etch is less specific to crystal defects rounding off the angularities caused by the oxygen etch (which aggressively attacks such defects) and provides a smoother, better surface for subsequent growth.

The surface or surfaces of the diamond substrate on which the CVD diamond growth occurs are preferably the {100}, {110}, {113} or {111} surfaces. Due to processing constraints, the actual sample surface orientation can differ from these orientations by up to 5°, and in some cases up to 10°, although this is less desirable as it adversely affects reproducibility.

The dissociation of the source gas is preferably carried out using microwave energy in a reactor examples of which are known in the art. However, the transfer of any impurities from the reactor should be minimised. A microwave system may be used to ensure that the plasma is placed away from all surfaces except the substrate surface on which diamond growth is to occur and its mount, the substrate carrier. Examples of preferred mount materials are: molybdenum, tungsten, silicon and silicon carbide. Examples of preferred reactor chamber materials are stainless steel, aluminium, copper, gold, and platinum.

The second layer of boron doped single crystal diamond is preferably grown on the processed surface of the substrate layer by CVD techniques where the substrate layer is the substrate. The details for CVD synthesis are as defined above with the key exception that the surface of the substrate layer of boron doped single crystal diamond is not subjected to an anisotropic etching step. If an etch is performed at all, it is an isotropic etch.

Further layer(s) of single crystal diamond, preferably boron doped single crystal diamond, may be grown on the surface of the second layer of boron doped single crystal diamond.

The surface of the second layer of boron doped single crystal diamond (and/or third and/or subsequent layers, if present) may be (i) an unprocessed surface; (ii) an isotropically etched surface; (iii) a surface which has been mechanically processed and then isotropically etched; (iv) a surface which has been mechanically processed wherein the final step is a scaife polish, in particular using a scaife polishing process optimised for low surface damage; or (v) a mechanically processed surface. Preferably the surface of the second layer of boron doped single crystal diamond (and/or subsequent layer(s)) is (i) an unprocessed surface; (ii) an isotropically etched surface; or (iii) a surface which has been mechanically processed and then isotropically etched. More preferably, the surface of the second layer of boron doped single crystal diamond (and/or subsequent layer(s)) is (i) an unprocessed surface.

As used herein, the term "about x" is intended to include the value x itself.

The present invention is hereinafter described by reference to the following figures and examples which are in no way intended to limit the scope of protection claimed.

FIGS. 1(a) and 1(b) show rectangular and circular disc shaped electrodes.

Figure 1A:
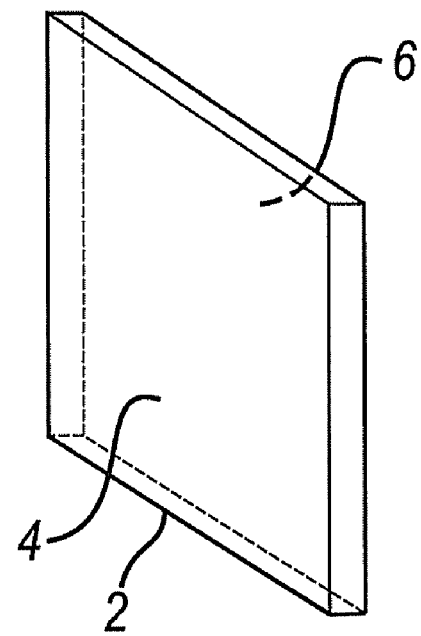
FIG. 1(a) shows a rectangular shaped solid diamond electrode (2) which may be used in an electrochemical cell. The electrode (2) has a first major working surface (4) and a second major working surface (6).
Figure 1B:
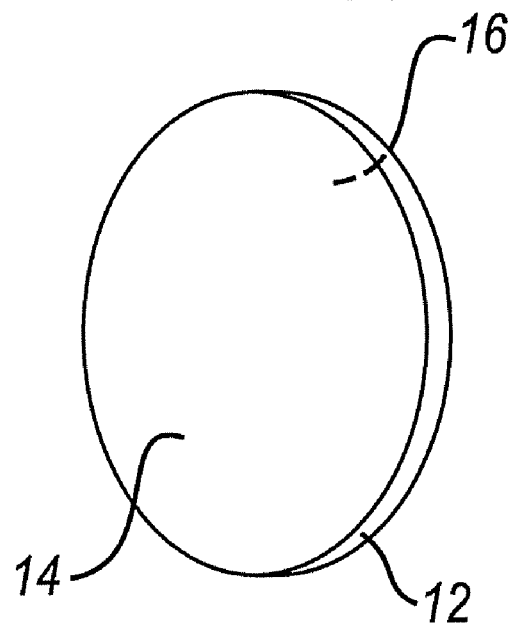
FIG. 1(b) shows a circular shaped solid diamond electrode (12) which may be used in an electrochemical cell. The electrode (12) has a first major working surface (14) and a second major working surface (16).
Figure 2:
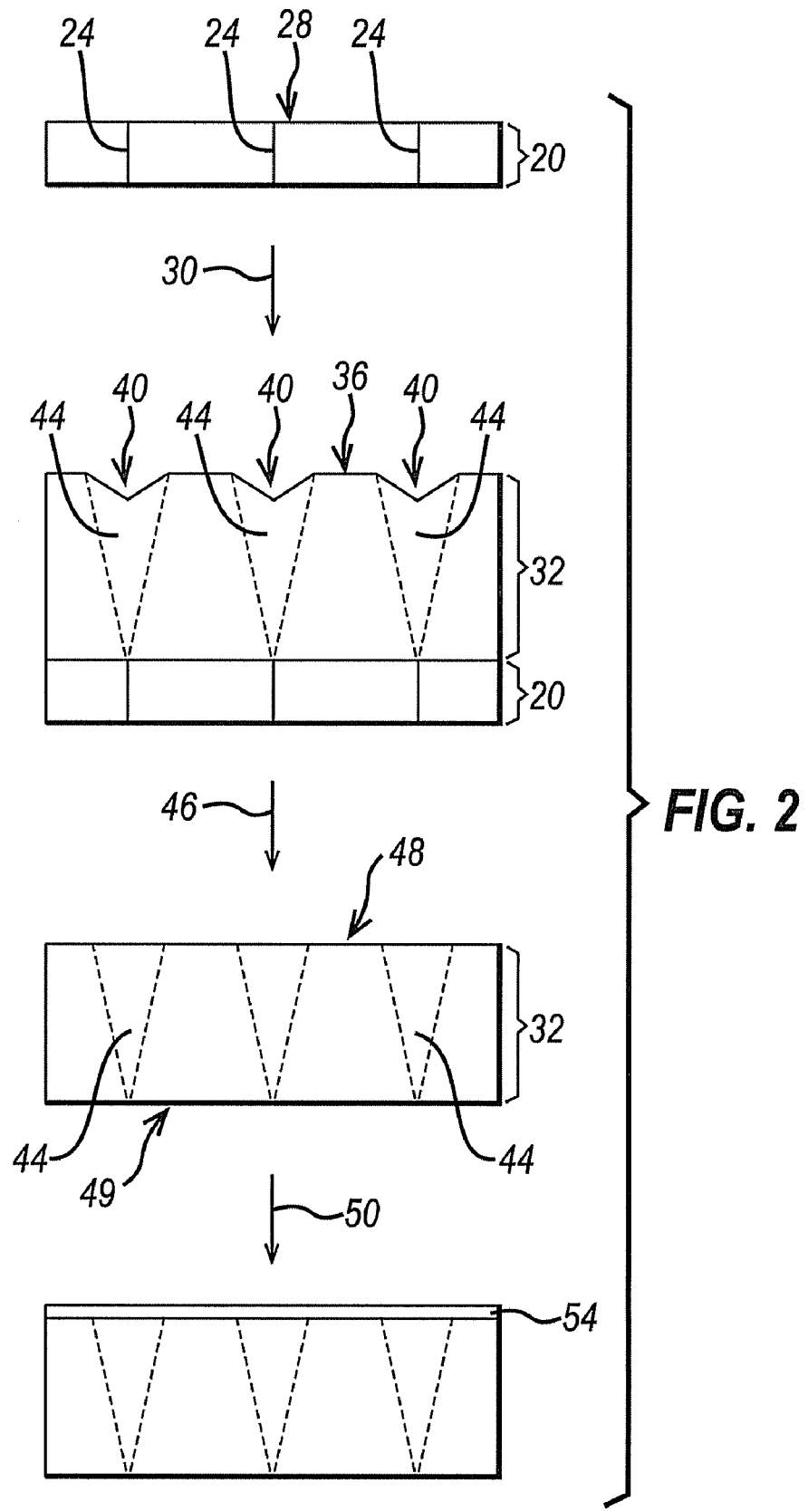
FIG. 2 illustrates an embodiment of the method of the present invention.

FIG. 2 is a schematic diagram of an embodiment of the method of the present invention. A single crystal diamond substrate (20) having a growth surface (28) suitable for use as a substrate for homoepitaxial CVD diamond is prepared. The substrate (20) is likely to contain dislocation bundles (24) that are aligned approximately perpendicular to the growth surface (28). A B-doped layer (32) is grown on the surface (28) of the substrate (20) using growth process 30. The surface of the as-grown B-doped layer (36) contains pits (40) that are underlain by volumes of reduced boron uptake (44) that are formed as the dislocations propagate during growth of the B-doped layer (32). The B-doped layer (32) is severed from the substrate (20) and is mechanically processed (46), using, for example, a diamond polishing scaif, forming surfaces (48) and (49). A thin B-doped layer (54) is grown on polished surface (48) to complete the electrode. Alternatively, the surface of the doped layer (54) is subjected to further processing such as isotropic etching or mechanical processing.

EXAMPLE

A high temperature/high pressure synthetic type 1b diamond was grown in a high pressure press, and prepared as a substrate using laser sawing, lapping and polishing to minimise sub-surface defects using a method of a revealing plasma etch to determine the defect levels being introduced by the processing the method. In this way, defects present in the substrate were minimised. A polished plate with lateral dimensions of about 7.65 mm×8.25 mm and with a thickness about 540 µm with all faces within 5° of {100} was produced. The surface roughness $R_q$ of the plate at this stage was less than 1 nm. The substrate was mounted on a tungsten substrate using a high temperature diamond braze.

The mounted substrate was introduced into a 2.45 GHz microwave plasma diamond synthesis system and an etch and growth cycle was commenced. The etch and growth cycle included the following steps:
1) An in situ oxygen plasma etch was performed using 15/75/600 sccm (standard cubic centimetre per second) of $O_2$/Ar/$H_2$ at a pressure of about $270\times10^2$ Pa and a substrate temperature of about 753° C. for a period of about 10 minutes.
2) This moved without interruption into a hydrogen etch with the removal of the $O_2$ from the gas flow at a temperature of about 758° C. for a period of about 10 minutes.
3) This moved into the growth process by the addition of the carbon source gas (in this case $CH_4$) and dopant gases, with the $CH_4$ flow of about 30 sccm. The B was added to the process as $B_2H_6$ using a calibrated source of nominally 100 ppm $B_2H_6$ in $H_2$ to simplify control. Additions of B are expressed as ppm, calculated for B as $[B_2H_6]/[\text{All gases}]$ where $[B_2H_6]$ represents the number of moles of $B_2H_6$ and [All gases] represents the number of moles of all gases present. The gas phase B concentration was 1.4 ppm $B_2H_6$. The substrate temperature at this stage was about 780° C. throughout the growth cycle.
4) The growth cycle was continued until the thickness of the layer reached approximately 1 mm thick.

On completion of the growth period, the substrate was removed from the reactor and the B-doped CVD diamond layer was removed from the substrate. At this stage in the process, the (001) growth surface of the B-doped CVD layer could be seen to have square and octagonal pits in the surface. The geometry of the pits indicates that the surfaces are {111} and {110} surfaces. The depth of the pits was highly variable, but most of the pits were around 10 to 20 µm in depth.

SIMS measurements of the growth surface of the B-doped CVD diamond layer showed that the average B concentration away from the pits is about $6.2\times10^{18}$ cm$^{-3}$. The B concentration in the pits is substantially lower at between about $5\times10^{17}$ cm$^{-3}$ and about $2\times10^{18}$ cm$^{-3}$.

While in this case, the B concentration is lower in the pits, the person skilled in the art will appreciate that, depending on the specific growth conditions, the reverse may be the case, i.e., the B concentration will be higher in the pits.

The B-doped CVD diamond layer was then processed by mechanical means (scaife polishing) to a plate about 735 µm thick and laser cut to lateral dimensions of about 5 mm×5 mm. Sufficient material was removed from the growth surface for there to be no pits visible in the surface as determined using a binocular microscope at a magnification of about 50×. The $R_q$ of the growth surface was better, i.e. lower than, about 1 nm. At this point imaging the growth surface with a DiamondView™ instrument showed that, although the pits had been removed, the boron concentration at the location of the pits was still substantially lower than elsewhere on the surface.

A further B-doped layer is then grown on the processed growth surface of the 735 µm thick plate using the same conditions as described in 3) above. This second growth process is terminated after approximately 2 µm of growth. This small amount of additional growth means that the surface does not require any further processing as pits at the top of dislocation plumes will not have developed at the surface of this thin layer.

Examination of the layer using DiamondView™ reveals that there are no regions of higher boron concentration present. SIMS measurements show that the boron concentration is about $5\times10^{18}$ cm$^{-3}$ and that there is no significant deviation from this value in the regions overlying the sites of the pits. Hence, the distribution of boron in the second growth layer, i.e. the conductive layer, is more uniform than the distribution of boron in the first layer, i.e. the substrate layer.

The electrode prepared in this method is found, by the use of a spatially resolved cyclic voltammetry probe, to have a spatially uniform electrochemical response, wherein, as a consequence of its more uniform distribution of boron, the electrical conductivity of the conductive layer is more uniform that the electrical conductivity of the substrate layer.

The invention claimed is:
1. Diamond material comprising a boron doped single crystal diamond substrate layer having a first surface and a boron doped single crystal diamond conductive layer on said first surface, wherein the distribution of boron in the conductive layer is more uniform than the distribution of boron in the substrate layer,
   wherein the average concentration of boron in the conductive layer is in a range from $1\times10^{18}$ atoms/cm$^3$ to $8\times10^{21}$ atoms/cm$^3$,
   wherein the average concentration of boron in the boron doped single crystal diamond substrate layer is in a range from $1\times10^{18}$ atoms/cm$^3$ to $8\times10^{21}$ atoms/cm$^3$, and
   wherein the conductive layer is CVD diamond and has a thickness of 100 µm or less.
2. Diamond material according to claim 1, wherein the electrical conductivity of the conductive layer is more uniform than the electrical conductivity of the substrate layer.
3. Diamond material according to claim 1, wherein the substrate layer is natural IIb diamond, high pressure high temperature (HPHT) synthetic IIb diamond or boron doped CVD diamond.
4. Diamond material according to claim 3, wherein the substrate layer is CVD diamond.
5. Diamond material according to claim 1, wherein the average concentration of boron in the substrate layer is in the range from $10^{18}$ to $5\times10^{21}$ atoms/cm$^3$.
6. Diamond material according to claim 1, wherein the average concentration of boron in the substrate layer is $1\times10^{21}$ atoms/cm$^3$ or less.

7. Diamond material according to claim 1, wherein the average concentration of boron in the conductive layer is in a range from $1\times10^{19}$ to $5\times10^{21}$ atoms/cm$^3$.

8. Diamond material according to claim 1, wherein the conductive layer has a thickness of 80 µm or less.

9. Diamond material according to claim 1, wherein the conductive layer has a thickness of 60 µm or less.

10. Diamond material according to claim 1, wherein the conductive layer has a thickness of 40 µm or less.

11. An electrode comprising diamond material as defined in claim 1, wherein an exposed surface of the conductive layer forms a major working surface of the electrode.

12. An electrochemical cell comprising an electrode as defined in claim 11.

13. An electrochemical sensor comprising an electrolyte and an electrode as defined in claim 11.

* * * * *